(12) United States Patent
Grosso

(10) Patent No.: US 7,001,350 B2
(45) Date of Patent: Feb. 21, 2006

(54) PORTABLE, INFLATABLE LUMBAR CUSHION

(76) Inventor: William M. Grosso, 2 Chestnut Park Ct., New City, NY (US) 10956

( * ) Notice: Subject to any disclaimer, the term of this patent is extended or adjusted under 35 U.S.C. 154(b) by 90 days.

(21) Appl. No.: 10/314,068

(22) Filed: Dec. 5, 2002

(65) Prior Publication Data

US 2003/0125650 A1   Jul. 3, 2003

Related U.S. Application Data

(63) Continuation-in-part of application No. 09/752,711, filed on Dec. 28, 2000, now abandoned.

(51) Int. Cl.
*A61F 5/00* (2006.01)
(52) U.S. Cl. .......................... 602/19; 128/876; 602/13
(58) Field of Classification Search ................. 602/19, 602/13; 128/870, 874–876; 2/311–313; 224/148.5, 660, 662
See application file for complete search history.

(56) References Cited

U.S. PATENT DOCUMENTS

| | | | | |
|---|---|---|---|---|
| 4,135,503 | A | * | 1/1979 | Romano ....................... 602/13 |
| 4,552,135 | A | * | 11/1985 | Racz et al. ................... 602/13 |
| 4,702,235 | A | * | 10/1987 | Hong ........................... 602/13 |
| 5,111,807 | A | * | 5/1992 | Spahn et al. ................ 606/244 |
| 5,122,111 | A | * | 6/1992 | Sebastian et al. ............. 602/19 |
| 5,179,942 | A | * | 1/1993 | Drulias et al. ........... 128/101.1 |
| 5,195,948 | A | * | 3/1993 | Hill et al. ..................... 602/19 |
| 5,205,814 | A | * | 4/1993 | Lundrigan et al. ............ 602/19 |
| 5,349,706 | A | * | 9/1994 | Keer .............................. 2/300 |
| 5,437,615 | A | * | 8/1995 | Pekar et al. .................. 602/19 |
| 5,450,858 | A | * | 9/1995 | Zablotsky et al. .......... 128/876 |
| 5,628,721 | A | * | 5/1997 | Arnold et al. ................ 602/19 |
| 6,331,170 | B1 | * | 12/2001 | Ordway ....................... 602/19 |

* cited by examiner

*Primary Examiner*—Stephen K. Cronin
*Assistant Examiner*—Fenn C. Mathew
(74) *Attorney, Agent, or Firm*—Brian L. Wamsley

(57) ABSTRACT

A portable, inflatable lumbar belt cushion for providing support to the lower spine and surrounding paralumbar musculature of the wearer while seated. The present invention is for an inflatable belt cushion which adjustably reinforces the small of the back to support the lower spine in a proper lorsdosis, alleviating lower back pain caused by improper posture and fatigue. The belt encircles the wearer's waist and contains a compartment with an inflatable cushion centrally located in the back of the belt which is superimposeable in the small of the wearer's back. The inflatable cushion is of a hemi-elliptical design which is positioned horizontally in the small of the back such that the thicker center portion of the cushion supports the spine and the thinner end portions support the surrounding musculature. The cushion extends outwardly from the outer surface of the belt and thus does not create a compression between the belt and the spine. Support is provided only when the wearer is seated and the cushion creates pressure between the wearer and the back of a chair. The cushion is inflated by manual means such that the firmness and pressure of the cushion is totally adjustable.

18 Claims, 4 Drawing Sheets

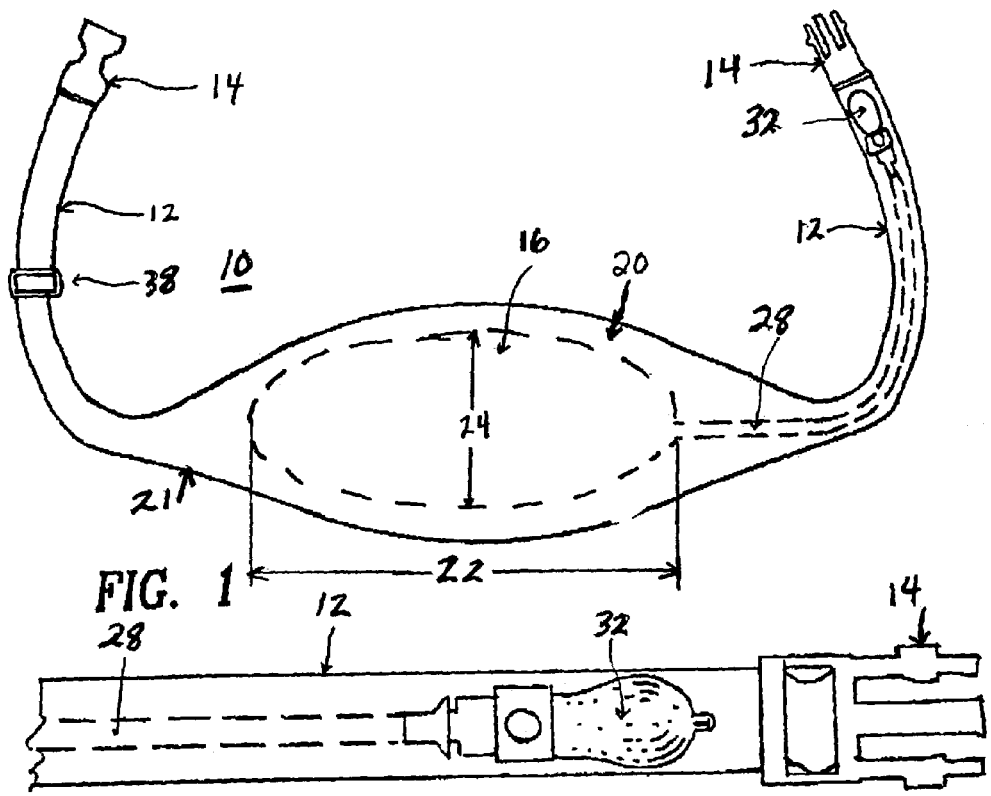
FIG. 1
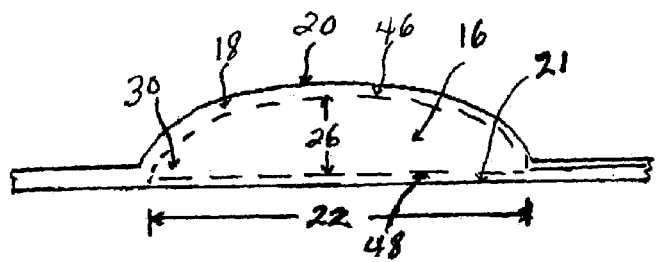
FIG. 2
FIG. 3

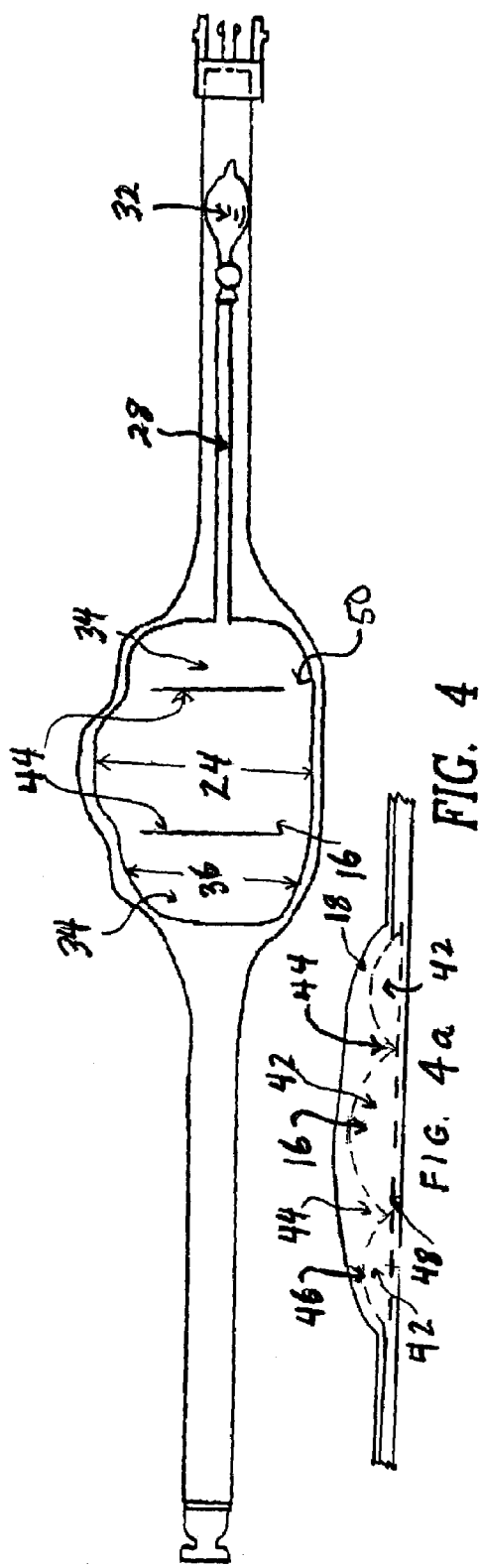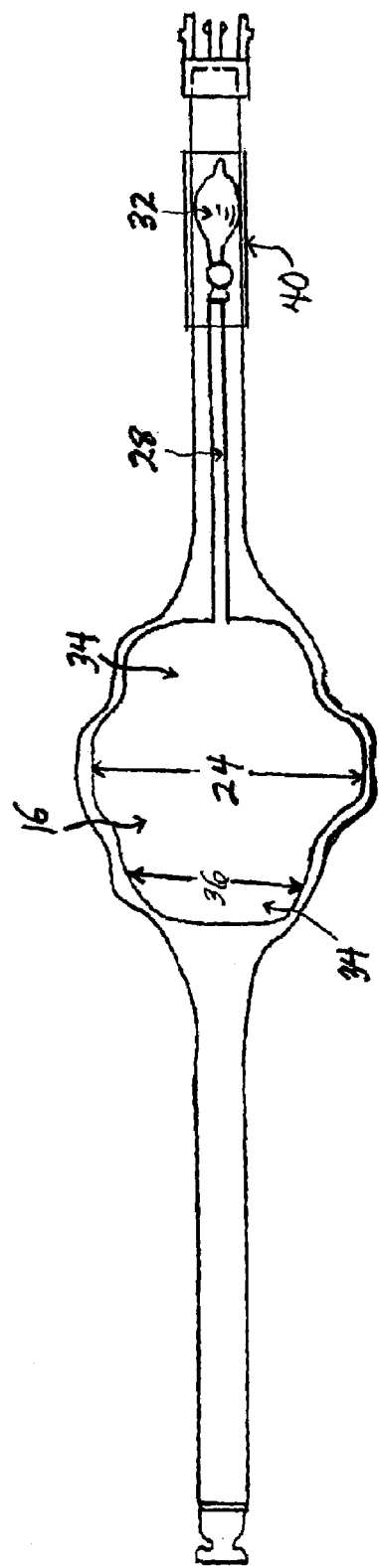

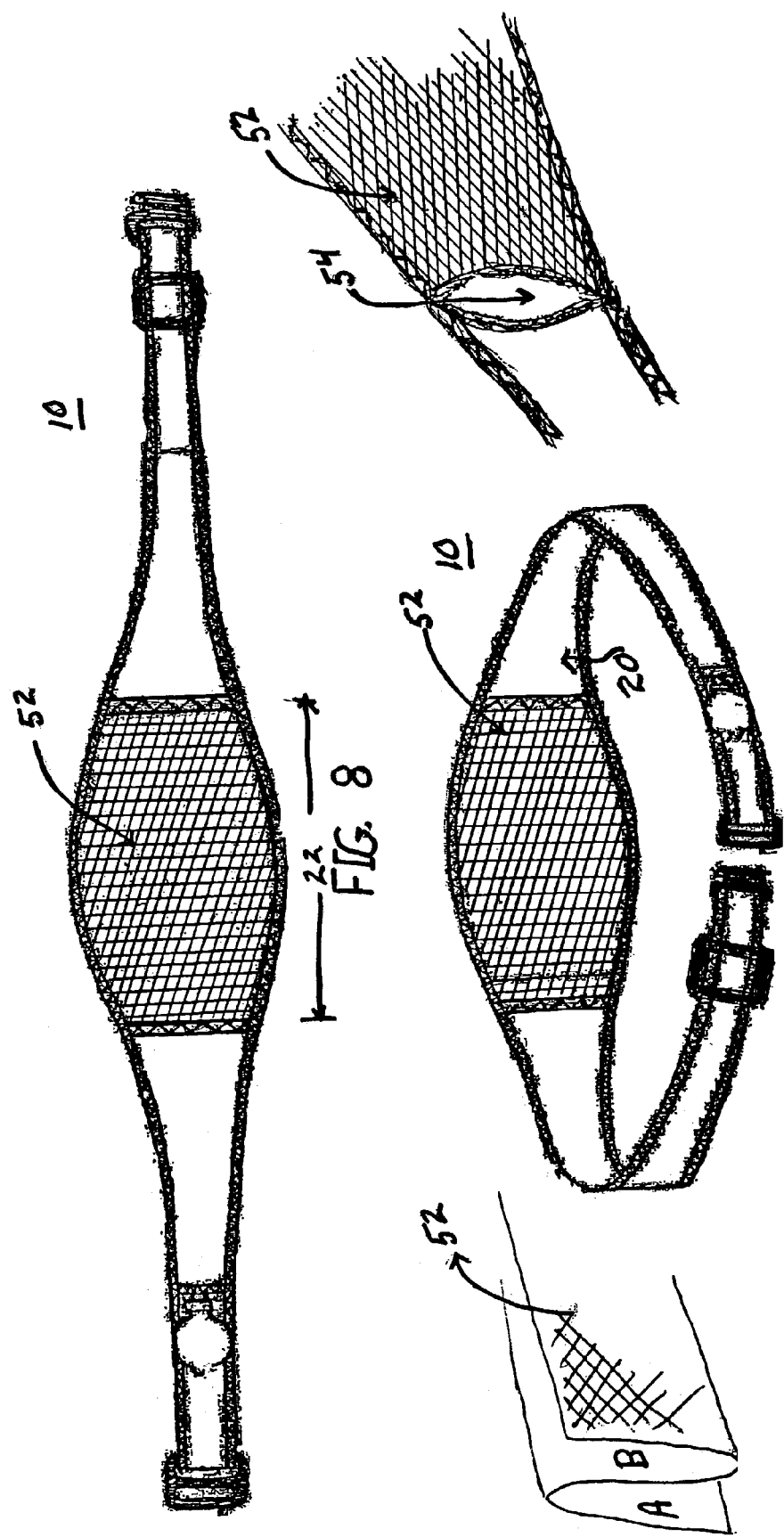

PORTABLE, INFLATABLE LUMBAR CUSHION

This is a continuation in part application of application Ser. No. 09/752,711, filed Dec. 28, 2000 now abandoned.

The present invention relates to a portable device capable of providing variable lower back support. More particularly, the invention relates to an inflatable, portable lumbar cushion which assists the spine being held in a proper forward curve position, or lordosis. The device comprises a portable, inflatable cushion, worn about the waist, having a particular configuration and dimensions to provide an individualized cushion when inflated. Inflating the lumbar cushion of this invention exerts pressure against a chair back when the wearer is seated, which in turn creates pressure against the lumbar vertebrae and the para-lumbar musculature to maintain the lower spine in a proper lordosis.

BACKGROUND OF THE INVENTION

Lower back pain is a serious problem in this country. It is estimated that eight out of ten Americans at one time or another will suffer from severe back pain. Most lower back pain from sitting is related to poor posture in which the person sits in a slumped or rounded posture. This poor posture occurs more readily when the seat or chair does not give proper support.

The position that we hold our spine when we sit is crucial to preventing or exacerbating back problems. The proper position is for the spine to be held in a forward curve called a lordosis. When a proper lordosis is maintained, there is less pressure on the lower back. This can be illustrated with regard to the lumbosacral angle, or Ferguson's angle, formed at the base of the spine. See Yochum, T. R. and Rowe, L. J., *Essentials of Skeletal Radiology*, Vol. 1, Williams & Wilkins, p.189 (1987). When the person is upright, the normal lumbosacral angle is 41°, with a standard deviation of ±7°. A decrease in the lumbosacral angle, such as when the lower back is becomes rounded when a person is seated in a slouched position, has been implicated as a mechanical factor in producing lower back pain by increasing disc pressure and placing undue stress on the lumbosacral posterior joints. Providing proper lower back support while seated would maintain the lumbosacral angle within its normal limits and thus alleviate lower back pain.

Numerous innovations for lower back supports have been known, such as spinal column supports having cushion material such as gaseous fluid or liquid fluid. Lower back cushions also exist in a variety of sizes, but are not adjustable and are generally inadequately designed to reduce the lumbosacral angle. Back supports which circumferentially enclose the body and the spine, in the form of a belt, are also known in the art. These devices are in the form of a back brace or support, most of which create compression around the waist and back to squeeze the spine, giving it support.

For example, prior art references provide back support means by which the supported area at the small of the back can be changed in a manner to effect varying degrees of support without having to change the construction of the pads or cushion. Romano, U.S. Pat. No. 4,135,503, discloses an orthopedic device which provides ambulatory traction to specific levels of the spine using an inflatable bladder. The bladder is affixed between a rigid base plate and an apertured template plate so as to extend outwardly from the base plate and inwardly toward the spine to create compression against a predetermined portion of the back and spine. The plates are mounted to a belt as well as brace strapping which is relatively unyielding when placed around the patient.

Eichler, U.S. Pat. No. 4,245,628, discloses a corset-like, back support bandage having a support pad with a fastening plate and an arch rib plate to which there is mounted an intermediate foam cushion. Racz et al., U.S. Pat. No. 4,552,135, discloses a belt for supporting the lower spinal column having a centrally located chamber in the rear of the belt filled with a sponge-like material. A valve connects the chamber with the atmosphere such that when the rear of belt is compressed, air is forced out. When the compression force on the chamber is removed, the sponge-like material forces the chamber walls apart, causing air to flow back into the chamber.

In contrast to the above-cited art, the present invention provides a back support especially suited for supporting the lower spinal column at the small of the back in a proper lordosis by employing a variably inflatable bladder or cushion of novel design arranged centrally respective to the small of the back. The cushion is configured and dimensioned to provide variable pressure and support to the L3, 4 and 5 vertebrae and the surrounding para-lumbar musculature when inflated. The cushion pushes against the back of a seat which in turn creates a counter pressure to the back. The novel, hemi-elliptical shape of the cushion results in the majority of the cushion being extended into the center of the spine while the outer portion pushes against the para-lumbar musculature of the lower spine and provides support across both sacro-iliac joints. The cushion is held into optimum position by a circumferentially extending belt which positions and holds the cushion within the small of the back. The size of the cushion and the air pressure within the cushion can be variably adjusted by the use of a manually operated air pump.

SUMMARY OF THE INVENTION

This invention is directed towards a portable, inflatable lumbar support device generally in the form of a removable belt designed to surround the waist of the human body. The belt properly positions an inflatable cushion or bladder at the proper level of the lower spine to provide support for the spine in a proper lordosis, when the wearer is seated. The inflatable cushion is positioned horizontally so that it provides lower back support to the spine as well as the surrounding para-lumbar musculature and the sacro-iliac joints located on each side of the lower spine. When inflated, the cushion has a hemi-elliptical shape so that more pressure or support to the spine and relatively less support to the musculature.

The back support apparatus in the form of a belt which includes a centrally positioned inflatable cushion. The rear of the belt curves into opposed elongated front straps, which terminate in a pair of spaced free ends. The marginal free ends of the front straps have fastener means associated therewith by which the ends can be attached to one another, thereby attaching the portable lumbar support to the wearer. An inflatable cushion is attached centrally to the center of the back belt portion and is of a size to be received against and provide support at the small of the back. The cushion includes an inflatable bladder attached to the outer surface of the center of the rear belt, and is contained in a pocket portion of the back belt. A tube connected with pump means controls the flow of air into and out of the inflatable cushion. The pump means is operated manually by the wearer whereby the amount of inflation and the internal air pressure within the cushion may be adjusted.

The inflatable cushion is generally oval in shape and is arranged horizontally in the center of the rear belt portion. The oval-shaped cushion is designed to have a specific lengthwise dimension such that, when inflated, the center of the cushion provides support to the spine while the ends of the cushion provide support for the para-lumbar musculature on either side of the spine and also contact and provide support to both sacro-iliac joints. The cushion also has a specific width dimension, as measured vertically through the center of the cushion, to provide support to the L3, L4 and L5 vertebrae. Additionally, the cushion has a particular depth dimension sufficient to cause a decrease in the lumbosacral angle to its normal limits.

Because the cushion is attached at the outer surface of the rear belt portion, when inflated, the cushion extends from the belt in an outward direction, as opposed to expanding inwardly from the belt toward the spine as found in the prior art, forming a hemi-elliptical shape. In addition, the cushion is designed to have an inflatable height dimension, measured in the center of the cushion, that is higher than the inflated height at the ends of the cushion. This novel design, unknown in the prior art, allows the cushion to provide more support to the center for the spine, and less support to the para-lumbar musculature. In one embodiment of the invention, the cushion is essentially divided into three sections, partially separated internally by heat sealing the front and back portions of the cushion, such that the partial separations help properly regulate the amount of inflation in the three individual sections.

The back support apparatus may also contain a sleeve or pocket located on the inside of the rear belt portion. The pocket is dimensioned to receive a device or insert, such as a heat pack or cold pack that are commercially available. An opening at one end of the pocket permits the removable insertion of the hot or cold pack which, when properly inserted and positioned, provides for heat or cold treatment at the lower spine. The hot or cold pack can be used regardless of whether or not the cushion is inflated The back support apparatus is meant to be continually worn by the user and is designed to appear as an ordinary waist pack of a type commonly worn in public, but may also be removed at will. This design permits for inconspicuous portability of the inflatable cushion. Nevertheless, the back support apparatus only provides lower back support when the wearer is seated, most often in chairs, couches, car seats or any other types of seat having a back.

In operation, the back support is placed on the wearer's body about the waist, arranged with the center of the rear belt lying against the wearer's back, and with the inflatable cushion positioned centrally respective to the small of the back. The elongated straps are brought about the abdomen and fastened together to thereby enclose the wearer's body. While the wearer is seated, the cushion is inflated using the pump means provided in the front of the belt portion. The firmness of the inflatable cushion, the amount of inflation and pressure exerted is dependent upon the particular person's comfort level. The cushion is inflated and becomes extended outwardly from the body until it contacts the back of the chair, for example and then exerts pressure against the back. The inflation is continued until the wearer feels that comfortable support is achieved in an optimum proper lordosis position. When the wearer rises to walk about, the pressure is automatically relieved from the cushion may be defalated by simply opening an air release valve.

A primary object of the present invention is the provision of a portable lumbar support having a variable volume and variable inflatable cushion associated therewith.

Another object of the present invention is the provision of a lumbar support having an elongated cushion positioned horizontally received against the small of the back, dimensioned such that the elongated cushion provides support to the L3, L4 and L5 vertebrae of the spine, and the para-lumbar musculature.

Still another object of the invention is the provision of a lumbar support which provides maximum comfort for the wearer in an optimum lordosis position of the spine, and wherein the volume and pressure of the cushion can be manually controlled by the wearer using pump means.

A further object of the invention is to provide a portable, adjustable lumbar support device wherein the lower portion of the spine can can be treated with heat or cold while the lower portion of the spine is held in the proper lordosis position.

The invention accordingly comprises the features of construction, combination of elements, and arrangement of parts which will be exemplified in the construction hereinafter set forth, and the scope of the invention will be indicated in the claims.

BRIEF DESCRIPTION OF THE DRAWINGS

For a fuller understanding of the nature and objects of the invention, reference should be had to the following detailed description of embodiments of the invention taken in connection with the accompanying drawings, in which:

FIG. 1 is a perspective view of the lower back support apparatus in accordance with the present invention;

FIG. 2 is a view of one end of the belt portion of the back support;

FIG. 3 is a top view of the central portion of the lower back support when inflated;

FIG. 4 is a front side view of an embodiment of the invention;

FIG. 4a. is a side view of the embodiment of FIG. 4;

FIG. 5 is a side view of a further embodiment of the invention;

FIG. 8 is a side view of a further embodiment of the invention; and

FIG. 9 is a perspective view of the lower back support apparatus in accordance with the embodiment of FIG. 8.

DETAILED DESCRIPTION OF THE INVENTION

Figure 6:
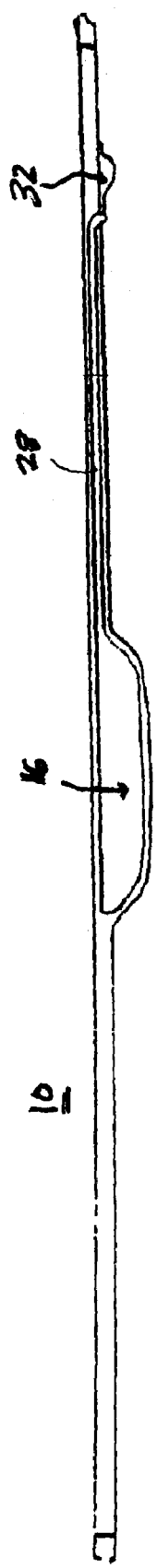
FIG. 6 is a top, cross-sectional view of the invention when deflated.

Referring now to the drawings wherein the showings are for purposes of illustrating different embodiments of the present invention and not for purposes of limiting the same, FIG. 1 perspectivley illustrates the portable, inflatable lumbar cushion in the form of a unitary belt 10 adapted to surround the wearer's waist, with a centrally positioned inflatable cushion 16. Cushion 16 is located inside a compartment 18, FIG. 3, having an outer side 20 and an inner side 21 made of a flexible fabric material or leather. The belt itself may be made of several layers of fabric-like material, or a rubber-type material such as neoprene, to form a relatively flexible belt apparatus which conforms to one's back and waist when properly fastened. The rear of the belt 10 curves into opposed elongated front straps 12 which terminate in a pair of spaced free ends 14 adapted to be attachable to each other. Free ends 14 are illustrated in the form of a pair of male-female clips of the type commonly used on a camper's backpack, but may be any type of device which permits attachability, such as belt buckle, velcro or the like. Additionally, the belt may contain a strap slide adjustment 38 for sizing the belt to individual users' waists.

Figure 7:
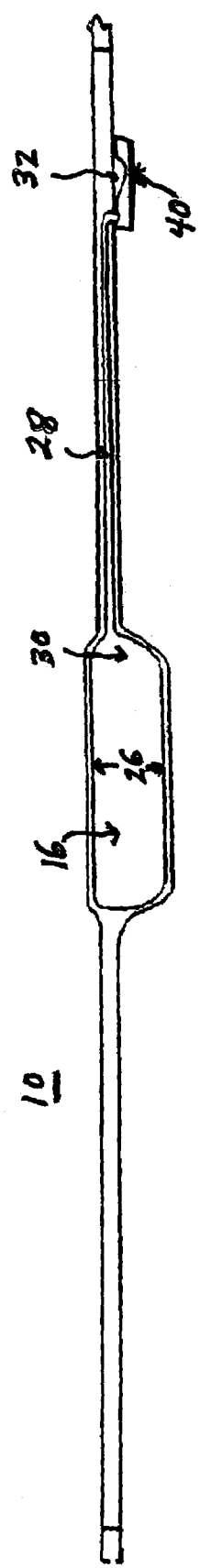
FIG. 7 is a top, cross-sectional view of the invention when inflated.

Cushion 16 is positioned horizontally within compartment 18 and is centrally located with respect to the length of the belt 10, so that when the belt 10 is properly attached about the waist, cushion 16 is centrally located in the small of the wearer's back. As shown in FIGS. 1 and 3, cushion 16 is generally oval in shape with its longer lengthwise dimension 22 being horizontally disposed. When inflated, cushion 16 expands outwardly from the outward side 20 of the belt 10 into a hemi-elliptical shape having a thickness dimension 26 at the center of the cushion which is generally thicker than at the ends 30 of the cushion 16. The difference in thickness between the center 26 of cushion 16 and the cushion ends 30 results in the hemi-elliptical shape of cushion 16, as seen from the top as in FIG. 3. However, the thickness of the cushion ends 30 may be increased as in other embodiments until it approaches the thickness of the center 26 of cushion 16, causing the profile to become more square as seen in FIG. 7.

Referring to FIGS. 1 and 2, a proximal end of flexible tube 28 is connected at one of the cushion ends 30 for providing a passageway for inflating and deflating cushion 16. Tube 28 may be manufactured from any flexible tubing material known in the art, such as synthetic or natural rubber, polyethylene, latex or the like. The distal end of tube 28 is connected to means 32 for inflating cushion 16. A manually operated squeeze bulb is preferred, although it is contemplated that other types of inflation means can be devised. Inflation means 32 is located on the outer surface of belt 10 at the end of one of front straps 12, so that inflation means 32 is easily accessible to the wearer when belt 10 is worn. Inflation means 32 can also be concealed within a pocket 40, FIG. 5, or by a piece of belt material folded over the belt and attached by velcro, or the like.

Being intended to provide lower back support by maintaining the lower spine in a proper lordosis position, cushion 16 is dimensioned to come into contact with specific anatomical points of the lower back. For example, the length dimension 22 of cushion 16 is selected to span the distance between the opposed sacro-iliac joints while providing support to the para-lumbar musculature. Accordingly, it has been found that a length 22 of 8 to 12 inches is sufficient to contact both sacro-iliac joints of most wearers, with 10 inches being preferred as the average. Similarly, cushion 16 has a center width dimension 24 of between 4 inches and 8 inches to contact the L3, L4 and L5 vertebrae, with 6 inches being the preferred average dimension. In order to maintain an adequate depth of an arc for a lordosis, cushion 16 may be inflated to a variable thickness, but optimally, a thickness 26 of only about 4 inches is necessary to create a proper lordosis. Additionally, a thickness of substantially greater than 4 inches could become uncomfortable to the average wearer.

FIGS. 4 and 5 depict further embodiments of the within invention. These embodiments may deviate from the general oval shape of cushion 16, to cushion shapes which provide proportionately variable support between the center along the spine, and lateral support for the paralumbar musculature. This variability is accomplished by increasing the cushion width dimension 36 near the cushion ends 30 over what would be the corresponding dimension for an oval shape. Accordingly, examples of these embodiments comprise cushion 16 having lateral support portions 34 with width dimensions 36 which are generally less than the width dimension 24 measured at the center of cushion 16. Width dimensions 34 may be varied, but are generally within the range of from 3 inches to 7 inches, which would still be less than width 24, but provide more or less support to the para-lumbar musculature as desired. It has been observed that, if the lateral portions 34 had the same width dimension 24 of the center of the cushion, the lower back would always be prevented from making close contact with the back of the chair. Portions of cushion 16 would not make complete contact with the chair, and would have nothing to push against to in turn push the lower spine forward into a proper lordosis. These variable width dimensions cause the unique cushion shapes as seen in FIGS. 4 and 5. The other dimensions of the cushion as herein described, would be within the limits discussed.

Additionally, the different shapes of cushion 16 in the embodiments may be designed to have different thickness in different parts of the cushion. As shown in FIGS. 4 and 4a, cushion 16 can be apportioned into multiple sections 42, with three sections being preferred. The sections 42 are separated by baffles 44, which may be formed by heat sealing the front side 46 of the cushion with the back side 48 of the cushion (see FIG. 3), or by any other similar means. The baffles extend for most of the width of cushion 16, but not not the entire width, leaving openings 50 between the sections 42 for the passage of air. In this manner, the baffles 44 regulate the levels of inflation among sections 42, permitting different thickness between the center and end sections.

FIG. 6 shows belt 10 where cushion 16 is deflated. Since cushion 16 does not contain any internal component to hold its shape, cushion 16 can be deflated to have essentially no thickness. When inflated, FIG. 7, the thickness 26 may any desired thickness, but 4 inches is the optimum thickness for the preferred embodiment of this invention. As a practical matter, once cushion 16 attains its maximum thickness, usually when the wearer is seated, adding additional air using inflation means serves to increase the firmness of the cushion.

FIGS. 8 and 9 illustrate an embodiment of the invention wherein mesh material 52 is utilized to form the belt 10, although as previously discussed, other types e of fabric, material or rubber material may be substituted for the mesh. The mesh material 52 can be folded and then stitched to create pockets A and B, which can be used, for example, for the insertion of the cushion 16 (not shown) or a hot or cold pack (also not shown). Typically, the cushion 16 would be located on the outer side of the belt 10, in pocket A, and the hot or cold pack would be inserted on the inner side of the belt 10, in pocket B. In that way, the hot/cold pack would directly contact the wearer's lower back in the proper position. Pockets A and B should be large enough the contain cushion 16 and a hot or cold pack, and it is preferred that the pockets extend the length 22 of the cushion, although pocket B could be shorter than that length if desired. An opening 54 may also be provided towards an end of the folded mesh material 52, for easy insertion of the hot/cold pack. Opening 54 could simply be an unstitched end of folded mesh material 52, or means for closing the opening 54, such as a zipper or Velcro® could be used.

While the present invention has been explained in relation to its preferred embodiment, it is to be understood that various modifications thereof will be apparent to those skilled in the art upon reading this specification. The invention disclosed herein is therefore intended to cover all such modifications that fall within the scope of the appended claims.

What is claimed is:

1. A lumbar belt back support apparatus for supporting the spine and para-lumbar musculature at the small of the wearer's back in a lordosis position while the wearer is seated, said support comprising;
   an elongated, circumferentially rigid extending belt portion having a pair of opposed belt ends adapted to be releasably placed about the person's waist, said belt portion having an inner surface and an outer surface;
   a compartment centrally located on the outer surface of the belt portion and positioned to be centrally adjacent the wearer's lower back when the opposed belt ends are connected, said compartment being configured to contain an inflatable bladder;
   a substantially oval inflatable bladder having a length, height and thickness dimensions provided inside said compartment, said length dimension of said bladder being positioned in a horizontal direction within the compartment;
   pump means for adjustably, manually inflating and deflating said bladder;
   tubing means for connecting said pump means with said bladder;
   wherein said bladder is configured to expand outwardly from said outer surface of said belt portion when manually inflated such that said bladder expansion causes compression between the wearer's back and the back of a chair or seat, causing pressure on the lower spine and back of the wearer; and
   wherein said bladder is configured as a hemi-elliptical shape such that more pressure is exerted on the lower spine than the surrounding para-lumbar musculature.

2. The lumbar belt according to claim 1, wherein the horizontal length dimension of the bladder is greater than the height dimension of the bladder.

3. The lumbar belt according to claim 2, wherein the horizontal length dimension is between 8 inches and 12 inches and the height dimension is between 4 inches and 8 inches.

4. The lumbar belt according to claim 3, wherein the horizontal length dimension is 10 inches and the height dimension is 6 inches.

5. A lumbar belt back support apparatus for supporting the spine and para-lumbar musculature at the small of the wearer's back in a lordosis position while the wearer is seated, said support comprising;
   an elongated, circumferentially rigid extending belt portion adapted to be releasably placed about the person's waist, said belt portion having an inner surface and an outer surface;
   a substantially oval inflatable bladder centrally located on the outer surface of the belt portion and positioned to be centrally adjacent the wearer's lower back when the belt portion is properly positioned about the person's waist, said inflatable bladder having a front side portion and a back side portion, and length, height and thickness dimensions, said length dimension of said bladder being positioned in a horizontal direction with respect to the belt portion;
   means for adjustably, manually inflating and deflating said bladder;
   wherein said bladder is configured to expand outwardly from said outer surface of said belt portion when manually inflated such that said bladder expansion causes compression between the wearer's back and the back of a chair or seat, causing pressure on the lower spine and back of the wearer; and
   wherein said bladder is configured as a hemi-elliptical shape such that more pressure is exerted on the spine than the surrounding para-lumbar musculature.

6. The lumbar belt according to claim 5, wherein the horizontal length dimension of the bladder is greater than the height dimension of the bladder.

7. The lumbar belt according to claim 6, wherein the horizontal length dimension is between 8 inches and 12 inches and the height dimension is between 4 inches and 8 inches.

8. The lumbar belt according to claim 7, wherein the horizontal length dimension is 10 inches and the height dimension is 6 inches.

9. The lumbar belt according to claim 5, further comprising a compartment centrally located on the outer surface of the belt, said compartment being configured to contain the inflatable bladder and positioned to be centrally adjacent the wearer's lower back when the belt is properly positioned about the wearer's waist.

10. The lumbar belt according to claim 9 wherein the inflatable bladder is positioned inside the compartment in a horizontal direction.

11. The lumbar belt according to claim 5 wherein said inflatable bladder is comprised of more than one inflatable compartments, said inflatable compartments being partially separated by baffles.

12. The lumbar belt according to claim 11 wherein said baffles are formed by heat-sealing the front side and back side portions of said inflatable bladder.

13. The lumbar belt according to claim 11 wherein said baffles are configured to regulate the flow of air between said compartments.

14. The lumbar belt according to claim 11 further comprising first, second and third inflatable compartments, wherein said second compartment is located between said first and third compartments, and said first and second compartments and said second and third compartments are separated by said baffles.

15. The lumbar belt according to claim 5, further comprising a second compartment centrally located on the inner surface of the belt and positioned to be located adjacent the wearer's lower back when the lumbar belt is properly positioned about the wearer's waist.

16. The lumbar belt according to claim 15 wherein said second compartment is configured as a pocket to contain an item.

17. The lumbar belt according to claim 15 wherein said second compartment is configured as a pocket to contain a cold pack or a heating pack.

18. A method of achieving a proper lordosis of the spine while seated, comprising the steps of;
   fastening a portable lumbar belt around one's waist, said lumbar belt comprising;
   an elongated, circumferentially extending belt portion having a pair of opposed belt ends adapted to be releasably placed about the person's waist, said belt portion having an inner surface and an outer surface;
   a compartment centrally located on the outer surface of the belt portion and positioned to be centrally adjacent the wearer's lower back when the opposed belt ends are connected, said compartment being configured to contain an inflatable bladder;
   a substantially oval inflatable bladder having a length, width and thickness dimensions provided inside said compartment, said length dimension of said bladder being positioned in a horizontal direction within the compartment;

pump means for adjustably, manually inflating and deflating said bladder;

tubing means for connecting said pump means with said bladder;

wherein said bladder is configured to expand outwardly from said outer surface of said belt when manually inflated such that said bladder expansion causes compression between the wearer's back and the back of a chair or seat, causing pressure on the spine and back of the wearer; and wherein said bladder is configured as a hemi-elliptical shape such that more pressure is exerted on the spine than the surrounding musculature; and manually inflating said bladder by operating the pump means until the expansion of the bladder causes a proper lordosis position to be achieved.

* * * * *